United States Patent [19]
Van Rees

[11] Patent Number: 6,066,293
[45] Date of Patent: May 23, 2000

[54] METHOD USING 5-CHLORO-2-(2,4-DICHLOROPHENOXY)PHENOL FOR DEODORIZING TOILETS

[75] Inventor: Norman A. Van Rees, Kirkwood, Mo.

[73] Assignee: Chemia Corporation, Kirkwood, Mo.

[21] Appl. No.: 08/982,568

[22] Filed: Dec. 2, 1997

Related U.S. Application Data

[63] Continuation of application No. 08/546,522, Oct. 20, 1995, Pat. No. 5,709,872.
[51] Int. Cl.[7] .............................. A61L 9/01; A61L 11/00; E03D 5/016
[52] U.S. Cl. .......................... 422/5; 424/76.7; 424/76.8; 4/222; 4/317
[58] Field of Search ......................... 422/5, 28; 424/76.1, 424/76.7, 76.8; 4/317, 222, 224, 225.1, 226.1, 227.1

[56] References Cited

U.S. PATENT DOCUMENTS

| | | |
|---|---|---|
| 3,897,357 | 7/1975 | Carmello et al. . |
| 4,017,395 | 4/1977 | Davis . |
| 5,286,719 | 2/1994 | Fost et al. . |

*Primary Examiner*—Elizabeth McKane
*Attorney, Agent, or Firm*—Armstrong Teasdale LLP

[57] ABSTRACT

A method for deodorizing toilets, and in particular the flushing fluid in a closed toilet system, comprises the use of phospholipids and 5-chloro-2-(2,4-dichlorophenoxy)phenol in the fluid to kill or inhibit odor-causing microbes.

25 Claims, 2 Drawing Sheets

METHOD USING 5-CHLORO-2-(2,4-DICHLOROPHENOXY)PHENOL FOR DEODORIZING TOILETS

This application is a continuation of U.S. patent application Ser. No. 08/546,522, filed Oct. 20, 1995, now U.S. Pat. No. 5,709,872.

This invention relates to deodorizing toilets, and in particular toilets which recirculate flushing fluid.

BACKGROUND OF THE INVENTION

In closed toilet systems, such as those used on airplanes, busses, and campers, the flushing fluid is recirculated. Recirculation of the flushing fluid requires that the used fluid be deodorized. Formaldehyde and glutaraldehyde have been used to disinfect flushing fluid. However, because of environmental concerns about the use of volatile organic compounds (VOCs), government regulations are increasingly restricting use of formaldehyde and glutaraldehyde.

Various attempts have been made to find alternative treatments for flushing fluids. Quaternary amines exhibit some antimicrobial action and thus have some ability to prevent the development of odors in the fluid, but are very irritating to the skin. Moreover, many of these compounds are corrosive, and their use in closed toilet systems is prohibited by many companies.

According to the principles of this invention, a toilet flushing fluid is made with phospholipids, and in particular synthetic phospholipids. These phospholipic compounds exhibit surfactant characteristics and are well tolerated by human tissue, i.e., they exhibit exceptionally low ocular irritation and oral toxicity. Synthetic phospholipids are generally characterized as having a quaternized alkyl amine groups and at least one phosphorus-containing anion in the molecule. Various synthetic phospholipids have been disclosed for example, in U.S. Pat. Nos. 4,215,064, 4,233,192 and 4,380,637 to Lindemann et al., U.S. Pat. Nos. 4,209,449, 4,336,385 and 4,503,002 to Mayhew et al., and U.S. Pat. Nos. 4,243,602, 4,283,542 and 4,336,386 to O'Lenick et al.

There is a need to provide a method for deodorizing the fluid used in closed toilet systems such as those used in airplanes, busses, and campers, which does not rely upon VOCs, is safe for human contact, does not corrode the fixtures, yet effectively prevents odors from developing in the fluid. Generally, the method for deodorizing toilets according to the present invention achieves these goals by providing an effective amount of phospholipid in the flushing fluid to kill or inhibit odor-causing microbes. The present invention provides a method of powerfully deodorizing the flushing fluid that complies with current environmental regulations, and is well tolerated by human tissue.

These and other features and advantages will be in part apparent, and in part pointed out hereinafter.

DETAILED DESCRIPTION OF PREFERRED EMBODIMENT

Figure 1:
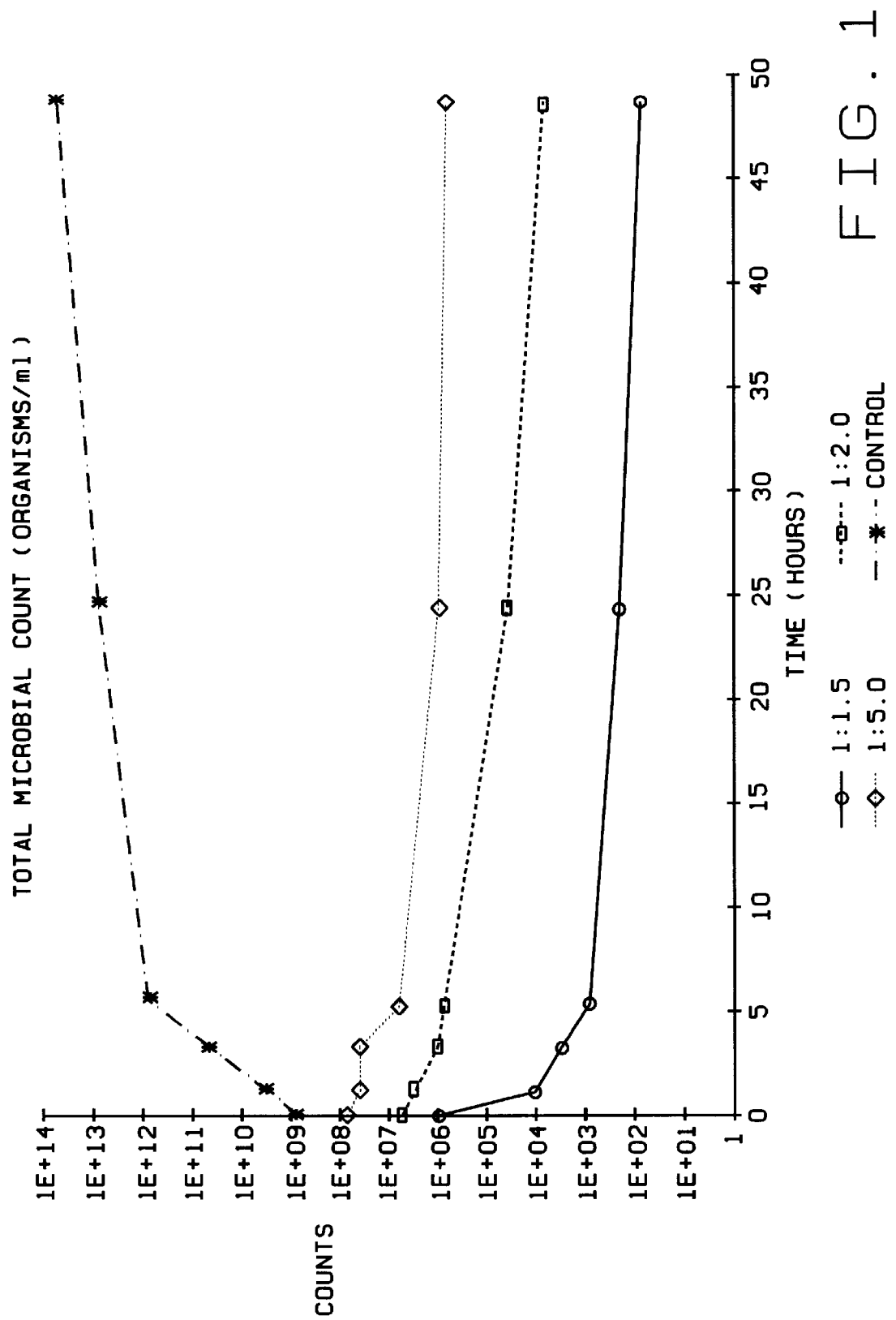
FIG. 1 is graph of microbial counts in various dilutions of a flushing fluid according to the principles of the present invention, showing the ability of these flushing fluids to control microbes.

The present invention provides for deodorizing toilets, and in particular for deodorizing the flushing fluid used in closed toilet systems, such as those used on airplanes, buses and campers. Generally, the method of this invention employs a toilet flushing fluid with a concentration of phospholipid effective to prevent odors from developing in the fluid by killing bacteria in the fluid or at least inhibiting the propagation of bacteria in the fluid. The flushing fluid may also contain a deodorant or scent to mask what odors do develop in the flushing fluid.

Examples of phospholipids useful in the present invention are as disclosed in U.S. Pat. Nos. 5,286,719, 5,215,976, 4,503,002 and U.S. Pat. No. 4,209,449, the disclosures of which are all incorporated herein by reference. Phospholipids useful in the present invention also include Phospholipid PTC™, Phospholipid EFA™, Phospholipid SV™, Phospholipid PTS, Phospholipid CDM™, Phospholipid PTL, and Phospholipid GLA available from Mona Industries, Inc., Paterson, N.J.

According to this invention, a phospholipid such as Phospholipid PTC™ is provided in the toilet flushing fluid in a concentration sufficient to kill or inhibit the propagation of odor-causing microbes. The phospholipid concentration is preferably between about 200 and about 7900 parts per million of the flushing fluid, and more preferably between about 400 and 2000 parts per million. Of course higher concentrations could be used but are believed to be unnecessary.

The flushing fluid is preferably formed by mixing a concentrate with tap water. A standard ratio is 1 oz. of concentrate per gallon of water, i.e., 1:128. The phospholipid preferably makes up between about 6.50 and about 20.00 percent by weight of the concentrate. Water preferably constitutes the majority of the concentrate, ranging between about 67.93 and about 89.70 percent by weight of the concentrate. The concentrate may also include fragrance, such as Clean & Fresh, #2257 available from Chemia, Inc., St. Louis, Mo., in an amount ranging from about 2.31 to about 7.00 percent by weight, to give the fluid a clean, fresh fragrance, and mask what odors do develop in the flushing fluid. In a portable toilet application, an appropriate light "potpourri"-type fragrance may be used. In an industrial or institutional application, such as a public rest room on an airplane, a strong or, more effective odor-neutralizing fragrance may be used, such as citronella, mint, or spice. When the concentrate is a liquid form, the fragrance is preferably an anhydrous or nearly anhydrous liquid selected from the group of essential oils, aroma chemicals, and odor neutralizers and masks. The fragrance is preferably, but not necessarily, a biodegradable substance. The concentrate preferably also contains alcohol, such as isopropyl alcohol, in an amount ranging from about 1.32 to about 2.00 percent by weight, to help solubilize fragrances. In addition, a coloring agent such as FD&C Blue #1 or Acid Blue #9 may be added to the concentrate in an amount preferably ranging from about 0.06 to about 0.07 percent by weight, to produce a deep blue color. A deep blue color is preferred because it best masks urine and other substances in the flushing fluid. The color, like the fragrance, is preferably, but not necessarily, a biodegradable substance. A detergent, such as Surfonic N95 or Surfonic N120 can be added to increase the detergency (cleaning capability) of the fluid. Additional anti-microbial agents such as triclosan 5-chloro-2-(2,4-dichlorophenoxy)phenol or ethylene glycol mono phenyl ether can be added to help control odor-causing microbes. The preferred concentration of triclosan in the flushing fluid is between about 1 and 20 parts per million. The preferred concentration of ethylene glycol mono phenyl ether is about 40 parts per million.

More specifically, the following are examples of concentrates useful in deodorizing toilets and in particular, airplane toilets, portable toilets and the like, according to this invention.

EXAMPLE 1

A toilet flushing fluid concentrate was prepared according to the following formula:

6.60 grams of Phospholipid PTC™ from Mona Industries, Inc. (cocamidopropyl phophatidyl polypropylene glycol-dimonium chloride)

1.32 grams of isopropyl alcohol 2.31 grams of Clean & Fresh Fragrance #2257 from Chemia Corporation 0.07 grams of FD&C Blue #1

89.7 grams of water.

The resulting concentrate is 6.6 weight percent phospholipid; 1.32 weight percent isopropyl alcohol; 2.31 weight percent of fragrance; 0.07 weight percent color; and 89.7 weight percent water.

EXAMPLE 2

A toilet flushing fluid concentrate was prepared according to the following formula:

20 grams of Phospholipid PTC™ from Mona Industries, Inc.

2 grams of isopropyl alcohol 7 grams of Spice Fragrance #2207 from Chemia Corporation 0.07 grams of FD&C Blue #1

3.0 grams of Surfonic N95

67.93 grams of water

The resulting concentrate is 20.0 weight phospholipid; 2.0 weight percent isopropyl alcohol; 7.0 weight percent fragrance; 0.07 weight percent color; 3.0 weight percent detergent; and 67.93 weight percent water.

EXAMPLE 3

A toilet flushing concentrate was prepared according to the following formula:

6.5 grams of Phospholipid PTC™ from Mona Industries, Inc.

1.3 grams of isopropyl alcohol 4.0 grams of Clean & Fresh™ Fragrance #2257 from Chemia Corporation 0.6 grams of Acid Blue #9

0.25 grams of triclosan 87.35 grams of water

The resulting concentrate was 6.5 weight percent phospholipid; 1.3 weight percent isopropyl alcohol; 4.0 weight percent fragrance; 0.6 weight percent color; and 0.25 triclosan; and 87.35 weight percent water.

EXAMPLE 4

A toilet flushing fluid concentrate was prepared according to the following formula:

7.0 grams of Phospholipid CDM™ from Mona Industries, Inc. (cocophosphatidyl polypropylene glycol-dimonium chloride)

4.0 grams of isopropyl alcohol 20 grams of Citrus Fragrance #3053 from Chemia Corporation 0.07 grams of FD&C Blue #1

1.0 gram of Surfonic N120

85.93 grams of water

The resulting concentrate is 7.0 weight percent phospholipid; 4.0 weight percent isopropyl alcohol; 3.5 weight percent fragrance; 0.07 weight percent color; 1.0 weight percent detergent; and 85.93 weight percent water.

EXAMPLE 5

A toilet flushing fluid concentrate was prepared according to the following formula:

8.0 grams of Phospholipid CDM from Mona Industries, Inc.

4.0 grams of isopropyl alcohol 3.5 grams of Spice Fragrance #2207 from Chemia Corporation 0.5 grams of ethylene glycol mono phenyl ether 1.0 gram of Surfonic N120

0.07 grams of FD&C Blue #1

82.97 grams of water

The resulting concentrate is 8.0 weight percent phospholipid, 4.0 weight percent isopropyl alcohol, 3.5 weight percent fragrance; 0.5 weight percent anti-microbial; 1 weight percent detergent; 0.07 weight percent color; and 82.97 weight percent water.

EXAMPLE 6

A toilet flushing concentrate prepared according to the following formula:

6.0 grams of Phospholipid CDM from Mona Industries, Inc.

4.0 grams of isopropyl alcohol 4.0 grams of citronella oil 0.60 grams of Acid Blue #9

0.25 grams of triclosan 1.0 grams of Surfonic N120

84.15 grams of water

The resulting concentrate is 6.0 weight percent phospholipid, 4.0 weight percent isopropyl alcohol, 4.0 weight percent fragrance (oil), 0.6 weight percent of Acid Blue #9; 0.25 weight percent anti-microbial agent; 1.0 weight percent detergent, and 84.15 weight percent water.

TEST

The concentrate of Example 1 was tested to determine its ability to control odors. The concentrate was diluted at a ratio of 1:128 with tap water to form a test fluid. At time zero, 200 mls of fresh raw sewage was added to 400 mls of the test fluid to create 600 mls of sample fluid at a dilution of 1:1.5. At the same time a control was prepared by mixing four parts of the fresh raw sewage with one part of tap water. After 30 minutes, the 1:1.5 sample fluid was divided into two equal portions of 300 mls each, and 100 mls of fresh raw sewage was added to one of these portions to create 400 mls of sample fluid at a dilution of 1:2. After 60 minutes, the 1:2 sample fluid was divided into two equal portions of 200 mls each, and 300 mls of fresh raw sewage was added to one of these portions to create 500 mls of a sample fluid at a dilution of 1:5. The sample fluids and the control were then incubated on a shaker at 35° C. Total microbial counts (organisms per ml) and total coliform counts (organisms/100 ml) were made of the various samples using standard techniques. These counts are tabulated in Table A:

| TOTAL MICROBIAL COUNT | | | | | | |
|---|---|---|---|---|---|---|
| DILUTION | 0 hr | 1 hr | 3 hrs | 5 hrs | 24 hrs | 48 hrs |
| 1:1.5 | $1 \times 10^6$ | $1 \times 10^4$ | $3 \times 10^3$ | $8 \times 10^2$ | $2 \times 10^2$ | $8 \times 10^1$ |
| 1:2.0 | $5 \times 10^6$ | $3 \times 10^6$ | $1 \times 10^6$ | $8 \times 10^5$ | $4 \times 10^4$ | $8 \times 10^3$ |
| 1:5.0 | $6 \times 10^7$ | $4 \times 10^7$ | $4 \times 10^7$ | $7 \times 10^6$ | $1 \times 10^6$ | $8 \times 10^5$ |
| CONTROL | $8 \times 10^8$ | $3 \times 10^9$ | $4 \times 10^{10}$ | $8 \times 10^{11}$ | $9 \times 10^{12}$ | $6 \times 10^{13}$ |

This information is indicated graphically in FIG. 1, showing that the diluted fluid affects the total microbial population, as compared with the control.

| TOTAL COLIFORM COUNT | | | | | | |
|---|---|---|---|---|---|---|
| DILUTION | 0 hr | 1 hr | 3 hrs | 5 hrs | 24 hrs | 48 hrs |
| 1:1.5 | $1 \times 10^5$ | $1 \times 10^3$ | $6 \times 10^2$ | $4 \times 10^2$ | $8 \times 10^1$ | $1 \times 10^1$ |
| 1:2.0 | $8 \times 10^6$ | $4 \times 10^6$ | $3 \times 10^4$ | $2 \times 10^4$ | $1 \times 10^4$ | $7 \times 10^2$ |
| 1:5.0 | $1 \times 10^8$ | $1 \times 10^7$ | $3 \times 10^6$ | $2 \times 10^6$ | $2 \times 10^5$ | $1 \times 10^3$ |
| CONTROL | $7 \times 10^8$ | $2 \times 10^9$ | $5 \times 10^9$ | $9 \times 10^9$ | $2 \times 10^{10}$ | $1 \times 10^{11}$ |

Figure 2:
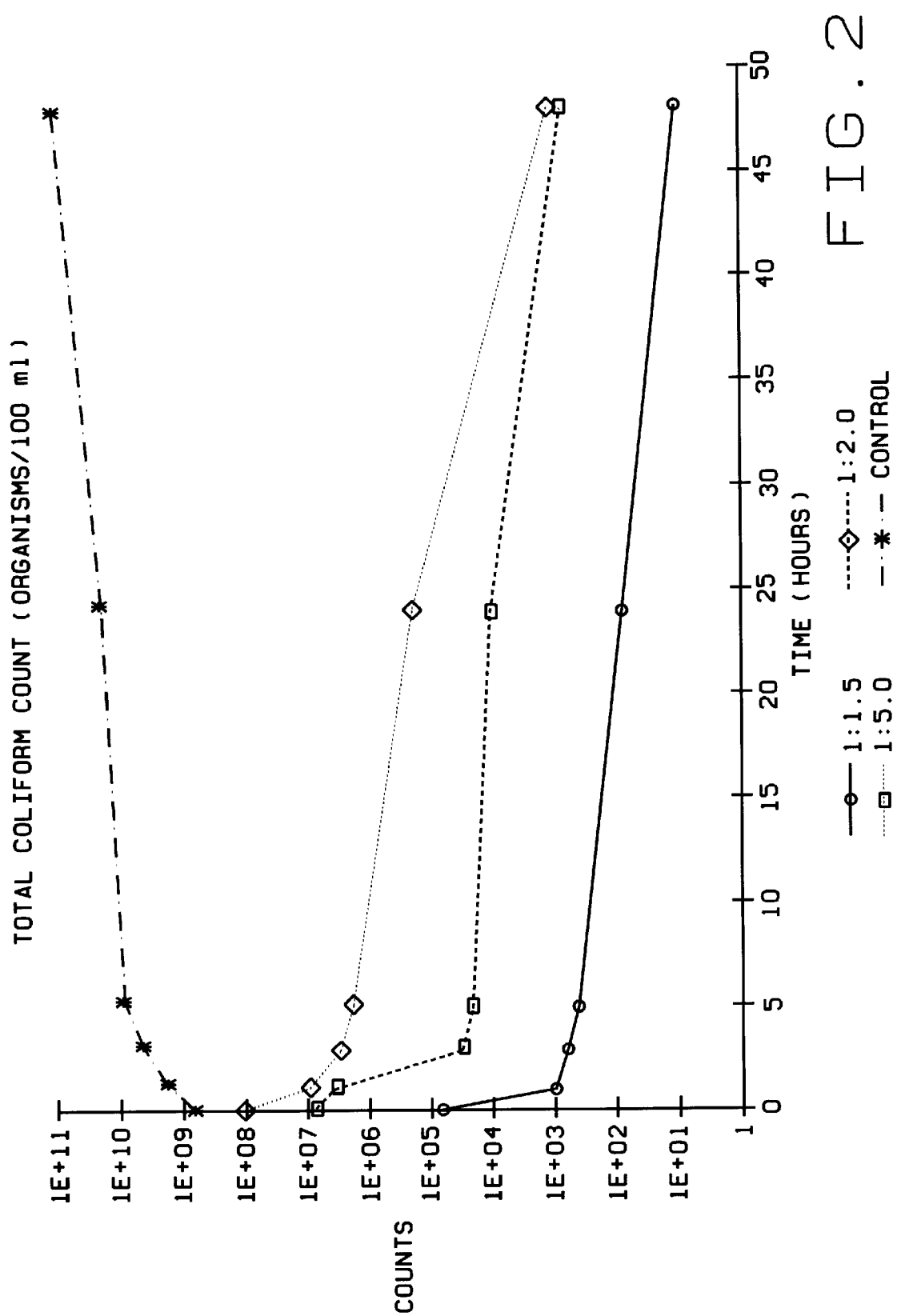
FIG. 2 is a graph of coliform counts in various dilutions of a flushing fluid according to the principles of the present invention, showing the ability of these flushing fluids to control microbes.

This information is indicated graphically in FIG. 2, showing that the diluted fluid affects the total coliform count, as compared with the control.

The 1:5 sample and the control were subjectively evaluated for order control on the following scale: 0=no odor; 1=slight odor; 2=moderate odor; 3=strong odor; and 4=very strong odor. The results are given in the table:

| ODOR TEST | | | | | | |
|---|---|---|---|---|---|---|
| DILUTION | 0 hr | 1 hr | 3 hrs | 5 hrs | 24 hrs | 48 hrs |
| 1:5.0 | 2 | 2 | 2 | 2 | 2 | 2 |
| CONTROL | 4 | 4 | 4 | 4 | 4 | 4 |

This shows that the diluted fluid is effective in controlling odors.

The fluid concentrates of the several examples are adapted for use in closed toilet systems. The concentrate can be diluted in a ratio of 1:128 (e.g., one ounce in one gallon of water). The phospholipids help kill or inhibit bacteria in the fluid to reduce or delay the formation of odors in the fluid so that the fluid can be recirculated. Additional anti-microbial agents can be included in the fluid to help control odor-causing microbes. The detergent increases the cleaning action of the fluid. The fragrance masks odors that do occur and the color also masks contaminants in the fluids. The fluid is non-corrosive and is well tolerated by human skin. However, when the used fluid is disposed of, the phospholipid is sufficiently diluted that it loses its bacteriostatic properties and becomes biodegradable. Thus while in use concentrations the phospholipids exhibit odor control capabilities, when diluted the phospholipids readily degrade.

From the foregoing, it will be seen that this invention is one well adapted to attain all the ends and objectives hereinabove set forth, together with advantages that are obvious and that are inherent to the invention. It will be understood that certain features and sub-combinations are of utility and can be employed without reference to other features and sub-combinations. This is contemplated by and is within the scope of the claims. Because many possible embodiments can be made of the invention without departing from the scope thereof, it is to be understood that all matter herein set forth is to be interpreted as illustrative and not in a limiting sense.

What is claimed is:

1. A method of deodorizing a closed toilet system of the type that recirculates the flushing fluid, the method comprising the step of adding an aqueous solution comprising a phospholipid, 5-chloro-2-(2,4-dichlorophenoxy)phenol, and from about 1.3 to 4.0 percent by weight alcohol to the flushing fluid in a concentration effective to inhibit odor-causing bacteria.

2. The method according to claim 1 wherein the phospholipid is cocamidopropylphophatidyl polypropylene glycol-dimonium chloride.

3. The method according to claim 1 wherein the phospholipid is cocophosphatidyl polypropylene glycol-dimonium chloride.

4. The method according to claim 1 further comprising the step of adding a fragrance to the flushing fluid.

5. The method according to claim 1 wherein the step of adding an aqueous solution comprising a phospholipid, 5-chloro-2-(2,4-dichlorophenoxy)phenol, and from about 1.3 to 4.0 percent by weight alcohol to the flushing fluid comprises the step of adding a flushing fluid concentrate comprising an aqueous solution comprising a phospholipid, 5-chloro-2-(2,4-dichlorophenoxy)phenol, water, and from about 1.3 to 4.0 percent alcohol to the flushing fluid.

6. The method according to claim 5 wherein the concentrate further includes a fragrance.

7. The method according to claim 5 wherein the alcohol comprises isopropanol.

8. The method according to claim 5 wherein the concentrate further includes a colorant.

9. The method according to claim 5 wherein the concentrate further comprises a detergent.

10. A method of deodorizing the flushing fluid in a closed toilet system in which the flushing fluid is recirculated, the method comprising the step of adding an aqueous solution comprising a phospholipid, 5-chloro-2-(2,4-dichlorophenoxy)phenol and from about 1.3 to 4.0 percent by weight alcohol to the flushing fluid in a concentration effective to inhibit odor-causing bacteria.

11. The method according to claim 10 wherein the phospholipid is cocamidopropylphophatidyl polypropylene glycol-dimonium chloride.

12. The method according to claim 10 wherein the phospholipid is cocophosphatidyl polypropylene glycol-dimonium chloride.

13. The method according to claim 10 further comprising the step of adding a fragrance to the flushing fluid.

14. The method according to claim 10 wherein the step of adding an aqueous solution comprising a phospholipid, 5-chloro-2-(2,4-dichlorophenoxy)phenol, and from about 1.3 to 4.0 percent by weight alcohol to the flushing fluid comprises the step of adding a flushing fluid concentrate comprising an aqueous solution of a phospholipid, 5-chloro-2-(2,4-dichlorophenoxy)phenol, water, and from about 1.3 to 4.0 percent by weight alcohol to the flushing fluid.

15. The method according to claim 14 wherein the concentrate further includes a fragrance.

16. The method according to claim 14 wherein the alcohol comprises isopropanol.

17. The method according to claim 14 wherein the concentrate further includes a colorant.

18. The method according to claim 14 wherein the concentrate further comprises a detergent.

19. A flushing fluid concentrate adapted to be added to the flushing fluid in a closed toilet system of the type in which the flushing fluid is recirculated, to control odors in the flushing fluid, said concentrate comprising an aqueous solution of a phospholipid, 5-chloro-2-(2,4-dichlorophenoxy) phenol, and from about 1.3 to 4.0 percent by weight alcohol.

20. The concentrate according to claim 19 wherein said alcohol comprises isopropanol.

21. A flushing fluid concentrate adapted to be added to the flushing fluid in a closed toilet system of the type in which the flushing fluid is recirculated, to control odors in the flushing fluid, said concentrate comprising an aqueous solution of a phospholipid, 5-chloro-2-(2 4-dichlorophenoxy) phenol, and from about 1.3 to 4.0 percent by weight alcohol.

22. The flushing fluid concentrate according to claim 21 wherein said phospholipid is cocamidopropylphophatidyl polypropylene glycol-dimonium chloride.

23. The flushing fluid concentrate according to claim 21 wherein said phospholipid is cocophosphatidyl polypropylene glycol-dimonium chloride.

24. An improved toilet flushing fluid for use in a recirculating flush toilet wherein said flushing fluid comprises an effective amount of an aqueous solution of a phospholipid, 5-chloro-2-(2,4-dichlorophenoxy)phenol, and from 1.3 to 4.0 percent by weight alcohol to control odor-causing bacteria.

25. An improved flush toilet system of the type that recirculates the flushing fluid, the improvement comprising an aqueous solution comprising a phospholipid, 5-chloro-2-(2,4-dichlorophenoxy)phenol, and from about 1.3 to 4.0 percent by weight alcohol in sufficient concentration to control odor-causing bacteria in the flushing fluid.

* * * * *

UNITED STATES PATENT AND TRADEMARK OFFICE
CERTIFICATE OF CORRECTION

PATENT NO. : 6,066,293
DATED : May 23, 2000
INVENTOR(S) : Norman A. Van Rees

It is certified that error appears in the above-identified patent and that said Letters Patent is hereby corrected as shown below:

On the title page item [54], and column 1, line 1, should read
--METHODS FOR DEODORIZING
TOILETS USING 5-CHLORO-2-(2,4-DICHLOROPHENOXY)PHENOL--.

Signed and Sealed this

Eighteenth Day of July, 2000

Attest:

Q. TODD DICKINSON

*Attesting Officer*   *Director of Patents and Trademarks*